(12) United States Patent
Tanaka et al.

(10) Patent No.: US 10,363,348 B2
(45) Date of Patent: Jul. 30, 2019

(54) CENTRIFUGAL PUMP

(71) Applicant: TERUMO KABUSHIKI KAISHA, Tokyo (JP)

(72) Inventors: Shotaro Tanaka, Kanagawa (JP); Yosuke Itamochi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 308 days.

(21) Appl. No.: 15/425,124

(22) Filed: Feb. 6, 2017

(65) Prior Publication Data

US 2017/0143884 A1 May 25, 2017

Related U.S. Application Data

(63) Continuation of application No. PCT/JP2015/073555, filed on Aug. 21, 2015.

(30) Foreign Application Priority Data

Sep. 19, 2014 (JP) ................................. 2014-191808

(51) Int. Cl.
| | |
|---|---|
| F04D 29/68 | (2006.01) |
| F04D 29/046 | (2006.01) |
| A61M 1/10 | (2006.01) |
| F04D 7/04 | (2006.01) |
| F04D 13/06 | (2006.01) |
| F04D 29/043 | (2006.01) |

(Continued)

(52) U.S. Cl.
CPC ............ *A61M 1/1013* (2014.02); *A61M 1/10* (2013.01); *F04D 7/04* (2013.01); *F04D 13/06* (2013.01);
(Continued)

(58) Field of Classification Search
CPC ..... F04D 7/00; F04D 7/02; F04D 7/04; F04D 29/043; F04D 29/046; F04D 29/0467;
(Continued)

(56) References Cited

U.S. PATENT DOCUMENTS

| | | | |
|---|---|---|---|
| 5,360,317 A | 11/1994 | Clausen et al. | |
| 5,458,459 A * | 10/1995 | Hubbard | ............. F04D 29/0413 |
| | | | 415/206 |

(Continued)

FOREIGN PATENT DOCUMENTS

| | | |
|---|---|---|
| EP | 1470832 A1 | 10/2004 |
| JP | 07075667 A | 3/1995 |

(Continued)

OTHER PUBLICATIONS

Supplementary European Search and Opinion Report, EP15841663, dated Feb. 16, 2018.
JPO Office Action dated May 24, 2017 for JP2016-548788.

*Primary Examiner* — Nathaniel E Wiehe
*Assistant Examiner* — Andrew J Marien
(74) *Attorney, Agent, or Firm* — MacMillan, Sobanski & Todd, LLC

(57) ABSTRACT

A centrifugal pump for pumping blood includes a housing 2 with a housing main body 20, a blood inlet port 25, and a blood outlet port 26. A rotary body 3 is rotatably accommodated inside the housing main body 20, and a support mechanism 4 supports the rotary body 3. The support mechanism 4 is provided with a rod-like shaft member 5, and a first bearing 6 and a second bearing 7 which respectively and rotatably support end portions of the shaft member 5. The first bearing 6 is provided with a protruding portion 62 which protrudes in an eccentric manner with respect to a rotation center O when viewed from an upstream side of a blood flow, so that the protruding portion shields a counter-rotating, longitudinal side of the shaft member from exposure to the main flow of blood.

7 Claims, 5 Drawing Sheets

(51) Int. Cl.
  *F04D 29/42* (2006.01)
  *F04D 29/66* (2006.01)
  *A61M 1/12* (2006.01)
(52) U.S. Cl.
  CPC ......... *F04D 29/043* (2013.01); *F04D 29/046* (2013.01); *F04D 29/0467* (2013.01); *F04D 29/4273* (2013.01); *F04D 29/669* (2013.01); *F04D 29/688* (2013.01); *A61M 1/101* (2013.01); *A61M 1/122* (2014.02); *A61M 2206/20* (2013.01)
(58) Field of Classification Search
  CPC .. F04D 29/605; F04D 29/628; A61M 1/1013; A61M 1/10; A61M 2206/20; A61M 1/122; A61M 1/101
  See application file for complete search history.

(56) References Cited

U.S. PATENT DOCUMENTS

| | | | | |
|---|---|---|---|---|
| 5,588,812 | A | * | 12/1996 | Taylor ................. F04D 13/0646 415/900 |
| 5,601,418 | A | | 2/1997 | Ohara et al. |
| 5,713,730 | A | * | 2/1998 | Nose .................... F04D 29/0465 417/423.12 |
| 5,863,179 | A | | 1/1999 | Westphal et al. |
| 9,511,178 | B2 | * | 12/2016 | Naidyhorski ......... F04D 25/026 |
| 10,143,787 | B2 | * | 12/2018 | Kumano ............. A61M 1/3666 |
| 2003/0105420 | A1 | * | 6/2003 | Hubbard ............. A61M 1/3666 604/6.11 |
| 2006/0084836 | A1 | * | 4/2006 | Hubbard ............. A61M 1/3627 600/16 |
| 2013/0251516 | A1 | * | 9/2013 | Tanaka ..................... F04D 1/00 415/203 |
| 2016/0208804 | A1 | * | 7/2016 | Kumano .................. F04D 1/00 |
| 2016/0281743 | A1 | | 9/2016 | Itamochi |
| 2017/0122337 | A1 | | 5/2017 | Itamochi |
| 2017/0146030 | A1 | * | 5/2017 | Furukawa ............. B23K 26/18 |

FOREIGN PATENT DOCUMENTS

| | | |
|---|---|---|
| JP | 2001178816 A | 3/2001 |
| JP | 2003062065 A | 3/2003 |
| JP | 2007222670 A | 9/2007 |
| JP | 2013053591 A | 3/2013 |
| WO | 2012115184 A1 | 8/2012 |
| WO | 2015098709 A1 | 2/2015 |

* cited by examiner

CENTRIFUGAL PUMP

CROSS REFERENCE TO RELATED APPLICATIONS

This application is a continuation of PCT Application No. PCT/JP2015/073555, filed Aug. 21, 2015, based on and claiming priority to Japanese application no. 2014-191808, filed Sep. 19, 2014, both of which are incorporated herein by reference in their entirety.

The present invention relates to a bearing support for an impeller shaft in a centrifugal pump.

BACKGROUND OF THE INVENTION

In the related art, as blood pumps which transport blood, there have been known turbo-type pumps which send out blood in response to centrifugal force. The turbo-type pump includes a hollow housing, an impeller that is rotatably accommodated inside the housing, a rotary axis (i.e., shaft member) that serves as a rotation center of the impeller, an upper portion bearing that rotatably supports an upper end portion of the rotary axis, and a lower portion bearing that rotatably supports a lower end portion of the rotary axis (see, e.g., Japanese patent 4548450).

In the blood pump disclosed in Japanese patent 4548450, the housing is provided with an inlet port through which blood flows in, and an outlet port through which blood flows out. The inlet port and the outlet port are tubularly formed so as to protrude from the housing. In addition, the inlet port is provided so as to be an extension of the shaft member such that a central axis thereof coincides with the rotational axis of the rotary shaft member.

Recently, blood pumps in which the inlet port is provided so as to include an inclined section with respect to the rotary axis have been adopted. The outer profile of the inclined inlet port intersects an intermediate portion of the shaft member, and the pump housing typically includes a recessed portion or pocket that is coaxially aligned with the shaft member at the middle of the inlet port and receives an upper bearing installed inside the recessed portion for the shaft member.

However, in such a configuration, a circulation flow (reverse flow) of blood in the same direction as the rotational direction thereof is generated as a result of viscous drag at the outer periphery of the shaft member. When the circulation flow runs into (meets) a flow of blood flowing down through the inlet port, a retained portion (i.e., stagnant portion) of the blood is generated inside the inlet port. As a result thereof, in a case where the blood pump is used for a long time, there is a possibility that a thrombus may be formed inside the recessed portion, particularly at an outer peripheral portion of the shaft member or upper bearing.

SUMMARY OF THE INVENTION

An object of the present invention is to provide a centrifugal pump in which a thrombus can be effectively prevented or restrained from being formed inside a blood inlet port.

Such an object is realized according to preferred embodiments of the present invention as described below.

A centrifugal pump includes a housing that is provided with a housing main body which is configured to define a hollow body cavity to provide a pumping chamber. A blood inlet port is formed so as to protrude from the housing main body, which communicates with the housing main body, and through which blood flows in. A blood outlet port is provided at a different radial position from that of the blood inlet port in the housing main body and through which blood flows out. A centrifugal force applying member (i.e., an impeller) is rotatably accommodated inside the hollow portion and rotates so as to apply centrifugal force to blood. A support mechanism (e.g., shaft member and bearings) supports the centrifugal force applying member such that the centrifugal force applying member can rotate with respect to the housing. The support mechanism is provided with a shaft member installed at a rotational center axis of the centrifugal force applying member. A first bearing is installed inside the blood inlet port and rotatably supports one end portion of the shaft member, and a second bearing rotatably supports the other end portion of the shaft member. The blood inlet port has a proximal portion coaxial with the rotational center of the centrifugal force applying member and has a connection portion upstream of the proximal portion which inclines with respect to the rotational center of the centrifugal force applying member. The first bearing is provided with a protruding portion which is formed so as to extend in an eccentric manner with respect to the upper end of the shaft member when viewed from an upstream position within the inclined connection portion of the blood inlet port. As used herein, "eccentric" means that the protruding portion has a semi-columnar shape which is disposed along one longitudinal side of the shaft member, leaving an opposite longitudinal side of the shaft member uncovered.

In the centrifugal pump according to the foregoing description, the protruding portion has a function of preventing a reverse flow of blood caused due to rotation of the shaft member inside the blood inlet port because the protruding portion shields a counter-rotating, longitudinal side of the shaft member from exposure to the main flow of blood.

In the centrifugal pump, the protruding portion is preferably positioned on a side of the shaft member where a direction in which the blood flows down inside the blood inlet port and a rotational direction of the outer surface of the shaft member oppose each other.

In the centrifugal pump, the protruding portion may preferably form a semi-columnar shape which covers one half of the circumference of the shaft member.

In the centrifugal pump, a connection portion of the blood inlet port forms a cylindrical shape having an axis which inclines with respect to the rotational axis of the impeller. The protruding portion of the first bearing has an inclined distal, outer edge which inclines in the same direction as an inner peripheral surface of the connection portion of the blood inlet port.

In the centrifugal pump, the blood inlet port is provided with a recessed portion into which the first bearing is installed. The inclined distal edge of the protruding portion is positioned at a distance equal to or less than a distance between the inner peripheral surface of the connection portion of the blood inlet port and the central axis of the connection portion of the blood inlet port (i.e., the radius of the connection portion).

The centrifugal pump may further include a flow straightening portion that is formed so as to protrude toward the upstream side beyond the first bearing of the inner peripheral portion of the blood inlet port in order to straighten a flow of blood.

According to the present invention, the first bearing is provided with the protruding portion which is formed so as to protrude in an eccentric manner with respect to the shaft member when viewed from the upstream side of a blood flow. Therefore, a first blood flow caused due to blood flowing down inside the blood inlet port can be prevented from running into (i.e., meeting) a second blood flow (i.e., counterflow) caused due to rotation of the shaft member. Accordingly, a stagnant region in which blood is retained can be prevented from occurring inside the blood inlet port. Therefore, a thrombus can be effectively prevented or restrained from being formed inside the blood inlet port.

DETAILED DESCRIPTION OF PREFERRED EMBODIMENTS

Hereinafter, a centrifugal pump according to the present invention will be described in detail based on suitable embodiments illustrated in the accompanying drawings.

<First Embodiment>

Figure 1:
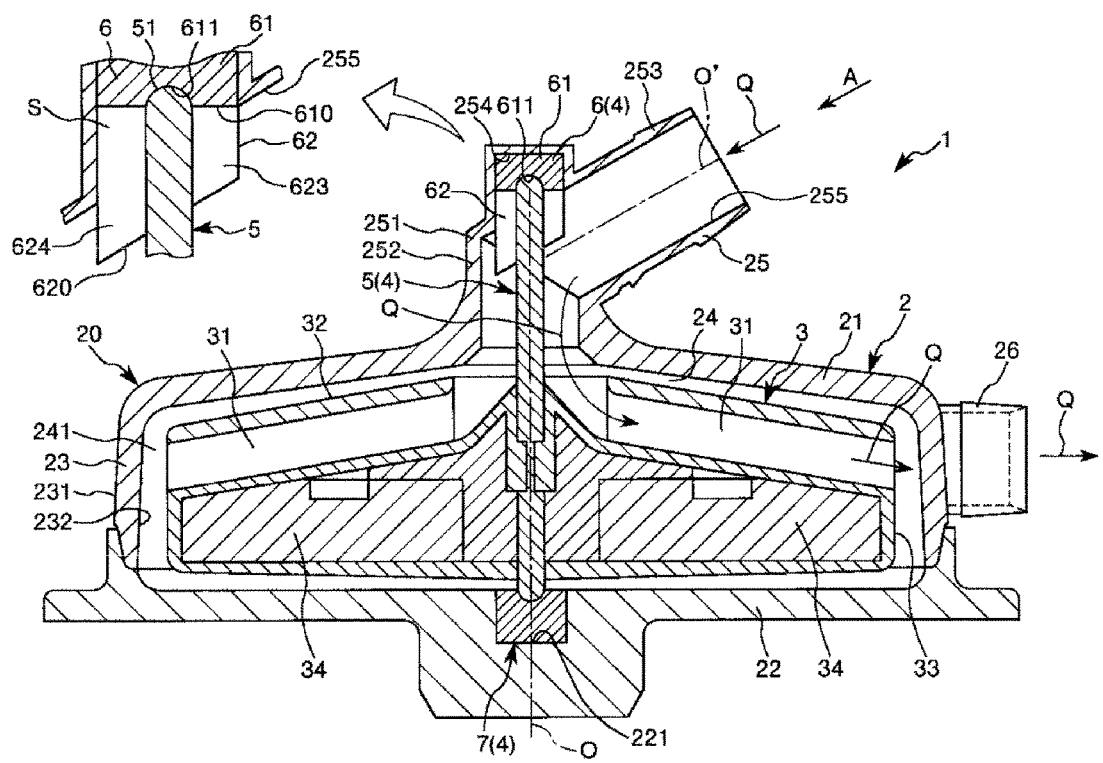
FIG. 1 is a cross-sectional side view illustrating an embodiment of a centrifugal pump according to the present invention.
Figure 2:
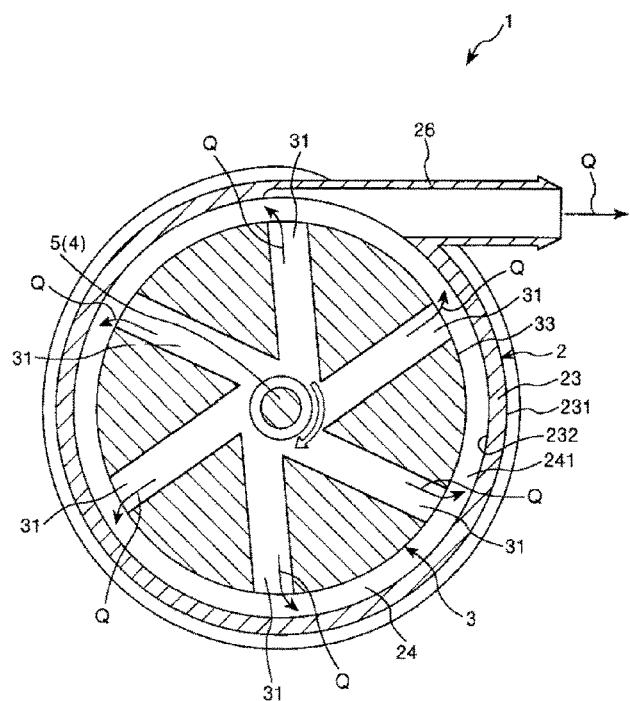
FIG. 2 is a cross-sectional plan view illustrating the embodiment of the centrifugal pump according to the present invention.
Figure 3:
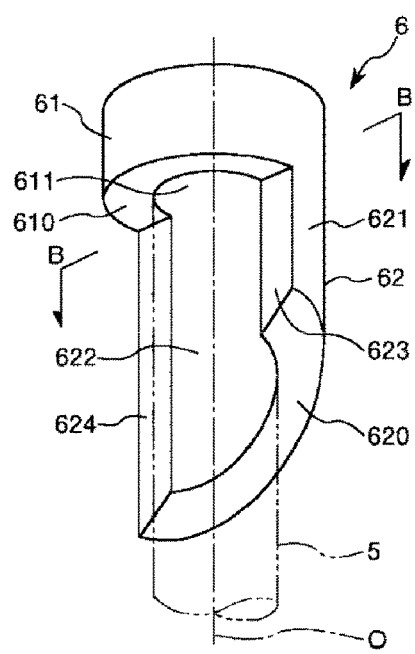
FIG. 3 is a perspective view of a first bearing included in the centrifugal pump illustrated in FIG. 1.
Figure 4:
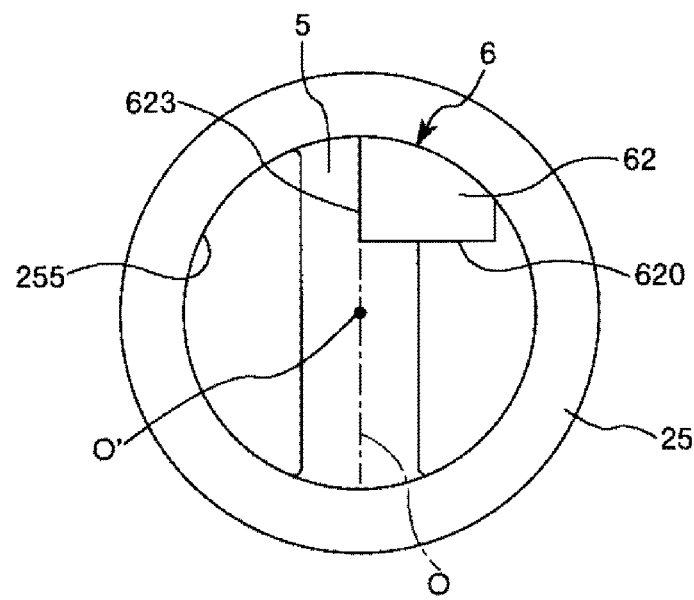
FIG. 4 is a view taken along arrow A in FIG. 1.
Figure 5:
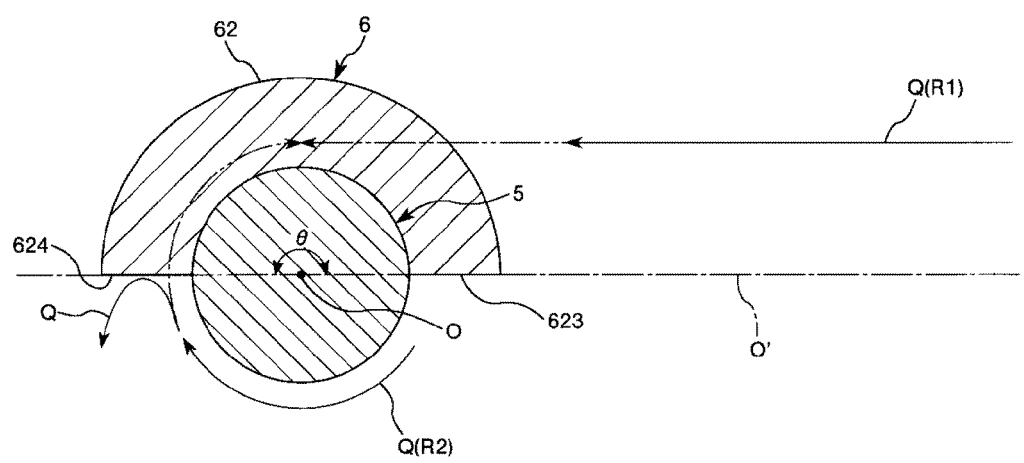
FIG. 5 is a cross-sectional view taken along line B-B in FIG. 3.

FIG. 1 is a cross-sectional side view illustrating an embodiment of the centrifugal pump, according to the present invention. FIG. 2 is a cross-sectional plan view illustrating the embodiment of the centrifugal pump, according to the present invention. FIG. 3 is a perspective view of a first bearing included in the centrifugal pump illustrated in FIG. 1. FIG. 4 is a view viewed in the arrow A direction in FIG. 1. FIG. 5 is a cross-sectional view taken along line B-B in FIG. 3.

Note that, hereinafter, for convenience of description, in FIGS. 1 and 3 (in FIGS. 5 to 9 as well), the upper side will be referred to as "up" or "upward", and the lower side will be referred to as "down" or "downward".

A centrifugal pump 1 illustrated in FIG. 1 includes a housing 2 which is configured to be a hollow body, a rotary body (impeller) 3 which is rotatably accommodated inside the housing 2, and a support mechanism 4 which supports the rotary body 3 such that the rotary body 3 can rotate with respect to the housing 2. Hereinafter, a configuration of each portion will be described.

The housing 2 is provided with a housing main body 20, a blood inlet port 25 through which blood Q flows in (such that blood Q is delivered to rotary body 3 in the area of its central rotational axis), and a blood outlet port 26 (receiving blood Q from an outer periphery of rotary body 3) through which the blood Q flows out.

The housing main body 20 is provided with a top plate 21 which is configured to be formed of a generally flat cylindrical member and blocks the upper end thereof, a side wall 23 which is erected from an edge portion of the top plate 21, and a bottom plate 22 which blocks the lower end. A flat space (hollow portion) surrounded by the top plate 21, the bottom plate 22, and the side wall 23 serves as a pump chamber 24.

The blood inlet port 25 and the blood outlet port 26 individually communicate with the pump chamber 24. The blood Q which has flowed in through the blood inlet port 25 can flow out through the blood outlet port 26 via the pump chamber 24.

As illustrated in FIG. 1, the blood inlet port 25 is tubularly (cylindrically) formed so as to protrude from a central portion of the top plate 21 (one end portion). A middle portion of the blood inlet port 25 in the longitudinal flow direction of port 25 is bent. A bent portion 251 defines a boundary portion of the blood inlet port 25 between a proximal portion 252 on the top plate 21 side and a connection section 253 on a side opposite thereto. Thus, proximal portion 252 and connection portion 253 generally define two intersecting cylinders with their central axes intersecting at bent portion 251. The connection section 253 is provided so as to incline with respect to a rotary axis O of the rotary body 3, and proximal portion 252 is coaxial with respect to the rotary axis of the rotary body 3. For example, a flexible tube for conveying blood through a blood circuit can be connected to the connection section 253.

As illustrated in FIG. 2, the blood outlet port 26 is tubularly formed so as to protrude from the outer peripheral surface (outer peripheral portion) 231 of the side wall 23. The blood outlet port 26 protrudes toward a tangential direction of the outer peripheral surface 231 of the side wall 23.

Inside the pump chamber 24 of the housing main body 20, the rotary body 3 having a disk shape is concentrically disposed. The rotary body 3 is a centrifugal force applying member which rotates so as to apply centrifugal force to the blood Q.

As illustrated in FIG. 2, the rotary body 3 is provided with a plurality of blood flow paths 31 (six in the illustrated configuration) through which the blood Q passes. The blood flow paths 31 are formed radially from the center of the rotary body 3. In addition, portions of the blood flow paths 31 at the axial center of the rotary body 3 meet (intersect) each other and are open on an upper surface 32 of the rotary body 3. Meanwhile, the opposite ends of the blood flow paths 31 are open to an outer peripheral surface 33 of the rotary body 3. In addition, a gap 241 is formed between the outer peripheral surface 33 of the rotary body 3 and an inner peripheral surface 232 of the side wall 23 of the housing 2.

When the above-described rotary body 3 rotates clockwise around a shaft member 5 as illustrated in FIG. 2 in which the housing 2 is viewed from above, the blood Q flowing in through the blood inlet port 25 enters each of the blood flow paths 31 from the portion on the center side of the rotary body 3, and the blood Q flows down through the blood flow paths 31 upon reception of centrifugal force. The flowed-down blood Q flows out to the inside of the gap 241. Thereafter, the blood Q receives clockwise rotary force inside the gap 241 as illustrated in FIG. 2. When the blood Q arrives at the blood outlet port 26, the blood Q is reliably discharged through the blood outlet port 26.

As illustrated in FIG. 1, in the rotary body 3, magnets are respectively installed at portions of the blood flow paths 31 on the lower side. Note that, in the configuration illustrated in FIG. 1, a plurality of (for example, six) permanent magnets 34 are adopted. When the centrifugal pump 1 is driven, the bottom plate 22 of the housing 2 is caused to be the lower side such that the below-described shaft member 5 becomes parallel to the vertical direction, and the centrifugal pump 1 is mounted with external drive means (not illustrated). In this mounted state, the centrifugal pump 1 is used. For example, the external drive means is provided with a motor and a permanent magnet which is interlocked with the motor. The permanent magnet and the permanent magnets 34 built in the centrifugal pump 1 attract each other due to magnetic force. When the motor rotates in such a state, rotary force thereof is transferred via the magnets attracting each other, and thus, the rotary body 3 can also rotate.

Note that, the diameter of the rotary body 3 is not particularly limited. For example, the diameter preferably ranges from 20 to 200 mm and more preferably ranges from 30 to 100 mm. The thickness (i.e., vertical height) of the rotary body 3 is not particularly limited. For example, the thickness preferably ranges from 3 to 40 mm and more preferably ranges from 5 to 30 mm. The maximum speed of the rotary body 3 is not particularly limited. For example, the maximum speed preferably ranges from 2,000 to 6,000 rpm and more preferably ranges from 2,500 to 5,000 rpm.

In addition, the configuration material of the rotary body 3 and the housing 2 is not particularly limited. For example, it is possible to exemplify an acryl-based resin such as rigid polyvinyl chloride, polyethylene, polypropylene, polystyrene, polycarbonate, an acrylic resin, and polymethyl methacrylate (PMMA); polyester such as polyethylene terephthalate (PET) and polybutylene terephthalate (PBT); polysulfone; and various types of rigid resins such as polyarylate. In addition, among the above-referenced configuration materials, polycarbonate and an acrylic resin are particularly preferable in regard to the points of suitability with respect to the blood Q, and excellent transparency and molding processability.

As illustrated in FIG. 1, the rotary body 3 is supported via the support mechanism 4 so as to be rotatable with respect to the housing 2. The support mechanism 4 is provided with the shaft member 5, a first bearing 6 which rotatably supports the upper end portion (one end portion) of the shaft member 5, and a second bearing 7 which rotatably supports the lower end portion (the other end portion) of the shaft member 5.

The shaft member 5 is installed at the rotational center axis of the rotary body 3. The shaft member 5 is configured to be a rod-like member having both end portions rounded. In a case where ceramic is adopted as the configuration material of the shaft member 5, when the end portions of the shaft member 5 are subjected to grinding, sliding characteristics of both the end portions during rotation of the shaft member 5 are improved. In a case where a metallic material is adopted as the configuration material of the shaft member 5, both the end portions of the shaft member 5 may be coated with diamond-like carbon (DLC) or titanium, for example, to resist grinding. Accordingly, sliding characteristics and durability of both the end portions during rotation of the shaft member 5 are improved.

The first bearing 6 is fixedly installed in a first bearing installation portion (recessed portion) 254 which is formed so as to be recessed in an inner peripheral portion of the connection section 253 of the blood inlet port 25 (i.e., upstream of bent portion 251). The second bearing 7 is fixedly installed in a second bearing installation portion 221 which is formed so as to be recessed in the central portion of the bottom plate 22 of the housing 2. Note that, the method of fixing the first bearing 6 and the second bearing 7 with respect to the housing 2 is not particularly limited. For example, it is possible to exemplify a method performed through fitting, a method performed through gluing (gluing performed with a glue or a solvent), a method performed through welding (heat-welding, high-frequency welding, ultrasound welding, and the like), and a method performed through insert molding.

As illustrated in FIGS. 1 and 3, the first bearing 6 is provided with a support portion 61 which has a disk shape (columnar shape) and supports the shaft member 5, and a protruding portion 62 which is formed so as to protrude from the support portion 61.

The support portion 61 is provided in the bottom portion of the first bearing installation portion 254, and a lower surface 610 is retained within the first bearing installation portion 254. In addition, a cup-shaped support surface 611 to support the upper end portion of the shaft member 5 is formed in a central portion on the lower surface 610 of the support portion 61. The support surface 611 is depressed so as to be curved along the curved shape of an upper end surface 51 of the shaft member 5.

As illustrated in FIG. 3, the cross-sectional shape of the protruding portion 62 forms a semicircular arc covering a half the circumference of the upper end outer peripheral portion of the shaft member 5. In other words, a central angle θ of the cross-sectional shape of the protruding portion 62 is preferably about 180° (refer to FIG. 5). In addition, as illustrated in FIG. 4, when viewed from the upstream side of the blood inlet port 25, the protruding portion 62 is provided so as to be eccentric toward (i.e., disposed on) the right side with respect to the shaft member 5. If rotary body 3 were to be adapted to rotate in a direction opposite to that shown herein, then protruding portion 62 would instead be disposed on the left side with respect to the shaft member 5 to coincide with the area where an outer surface of shaft member 5 counter-rotates with respect to the incoming blood flow.

In addition, the apex surface (lower edge surface) 620 at the outer or distal edge of the protruding portion 62 inclines at an oblique angle. The apex surface 620 is positioned so as to be closer to a central axis O' of the connection portion 253 than an inner peripheral surface 255 in the radial direction of the blood inlet port 25. In addition, the apex surface 620 is provided so as to incline with respect to rotational center axis O of shaft member 5 in the same direction as the inner peripheral surface 255 of the blood inlet port 25 and at the same inclination angle. In other words, the apex surface 620 inclines along (i.e., is parallel to) the central axis O'. Accordingly, the protruding portion 62 can be prevented or restrained from inhibiting a blood flow of the blood Q (hereinafter, will also be referred to as "first blood flow R1") flowing down inside the blood inlet port 25. Therefore, the blood Q can smoothly flow down inside the blood inlet port 25.

In addition, as illustrated in FIGS. 1 and 3, the protruding portion 62 is provided with a first side surface 621, a second side surface 622, a third side surface 623, and a fourth side surface 624 all extending longitudinally parallel to the rotation center O. The first side surface 621 is configured to be the outer peripheral surface of the protruding portion 62. The second side surface 622 is configured to be the inner peripheral surface of the protruding portion 62 for receiving shaft member 5. The third side surface 623 is positioned on the upstream side of the shaft member 5. The fourth side surface 624 is positioned on the same plane as the third side surface 623 so as to be closer to the downstream side than the third side surface 623. In addition, the longitudinal length of the fourth side surface 624 (in the direction of rotational axis O) is longer than that of the third side surface 623.

As illustrated in FIG. 5, when the shaft member 5 rotates, a second blood flow R2 is caused around the shaft member 5 inside the blood inlet port 25. As mentioned above, since the shaft member 5 rotates clockwise when viewed from the upper side of the housing 2, the second blood flow R2 becomes a blood flow being wound clockwise around the shaft member 5.

As indicated with the two-dot chain line in FIG. 5, the second blood flow R2 would otherwise flow toward the upstream side on the upper side of the shaft member 5, that is, reversely flow when protruding portion 62 is not present. Therefore, the second blood flow R2 would meet, that is, run into the first blood flow R1 from the upstream side. When the flows run into each other, there would be cases where force of the blood Q is cancelled and a retention portion retaining the blood Q would be formed inside the blood inlet port 25. As a result thereof, there is a possibility that a thrombus would be formed inside the blood inlet port 25, particularly in the outer periphery of the shaft member 5 inside the first bearing installation portion 254.

In the centrifugal pump 1, as mentioned above, in the cross section illustrated in FIG. 5, the protruding portion 62 is provided so as to be biased on the upper side of the shaft member 5. Accordingly, the second blood flow R2 is blocked by the fourth side surface 624 of the protruding portion 62, that is, prevented from reversely flowing. Therefore, the second blood flow R2 and the first blood flow R1 which is flowing down can be prevented from running into each other, and thus, the retention portion can be prevented from being formed inside the blood inlet port 25. As a result thereof, a thrombus can be prevented or restrained from being formed inside the blood inlet port 25, particularly in the outer periphery of the shaft member 5 inside the first bearing installation portion 254.

In this manner, since the protruding portion 62 is provided at a portion where a direction in which the blood Q flows down inside the blood inlet port 25, and a rotational direction of the shaft member 5 are directions opposite to each other, a thrombus can be prevented or restrained from being formed in the outer periphery of the shaft member 5.

In addition, as illustrated in FIG. 1, since the protruding portion 62 is provided so as to be eccentric with respect to the rotation center O, a gap S is formed on a side opposite to the protruding portion 62 of the shaft member 5 inside the first bearing installation portion 254. Due to the second blood flow R2 caused inside the gap S, the blood Q which has entered a gap between the upper end surface 51 of the shaft member 5 and the support surface 611 is pushed out. Accordingly, the blood Q can be effectively prevented or restrained from being retained in the gap between the upper end surface 51 of the shaft member 5 and the support surface 611. As a result thereof, a thrombus can be prevented or restrained from being formed between the upper end surface 51 of the shaft member 5 and the support surface 611.

Note that, in the present embodiment, the central angle θ of the cross-sectional shape of the protruding portion 62 is 180°. However, the present invention is not limited thereto. For example, the central angle θ thereof may range from 90° to 270°, or the like.

It is preferable that the first bearing 6 and the second bearing 7 are configured to be formed of the same materials. In addition, the bearings and the shaft member 5 may be configured to be formed of the same materials as each other or may be configured to be formed of materials different from each other. In a case where the bearings and the shaft member 5 are configured to be formed of the same materials as each other, a rigid material is adopted as each of the configuration materials. For example, each of the first bearing 6, the second bearing 7, and the shaft member 5 can be configured to be formed of a metallic material or ceramic. In a case where the bearings and the shaft member 5 are configured to be formed of materials different from each other, a rigid material is adopted as the configuration material of the shaft member 5, and a material softer than the shaft member 5 is adopted as the configuration material of the bearings. For example, the shaft member 5 can be configured to be formed of a metallic material or ceramic, and each of the first bearing 6 and the second bearing 7 can be configured to be formed of a resin material.

The resin material is not particularly limited. For example, it is possible to exemplify polyethylene; polypropylene; polyolefin such as an ethylene-vinyl acetate copolymer; modified polyolefin; polyamide (for example: nylon 6, nylon 46, nylon 66, nylon 610, nylon 612, nylon 11, nylon 12, nylon 6-12, and nylon 6-66); thermoplastic polyimide; a liquid crystal polymer such as aromatic polyester; polyphenylene oxide; polyphenylene sulfide; polycarbonate; polymethyl methacrylate; polyether; polyether ether ketone; polyether imide; polyacetal; various types of thermoplastic elastomers such as a styrene-based elastomer, a polyolefin-based elastomer, a polyvinyl chloride-based elastomer, a polyurethane-based elastomer, a polyester-based elastomer, a polyamide-based elastomer, a polybutadiene-based elastomer, a trans-polyisoprene-based elastomer, a fluorine rubber-based elastomer, and a chlorinated polyethylene-based elastomer; and copolymers, blends, polymer alloys, and the like having these as a main ingredient. Among these, it is possible to adopt one type, or two or more types in a mixed state. Among these, it is particularly preferable to adopt polyethylene (super-high-molecular polyethylene) having a significant average molecular weight (for example, approximately two millions to ten millions). Particularly, when the first bearing 6 is configured to be formed of super-high-molecular polyethylene, abrasion resistance, processability, and self-lubricating characteristics of the first bearing 6 can be improved.

The metallic material is not particularly limited. For example, it is possible to exemplify stainless steel or the like. In addition to the metallic material, ceramic and the like can also be adopted. In addition, hardness (Vickers hardness (Hv)) of such a rigid material (the metal material, or ceramic) is not particularly limited. For example, the hardness is preferably 50 or greater and is more preferably 100 or greater.

<Second Embodiment>

Figure 6:
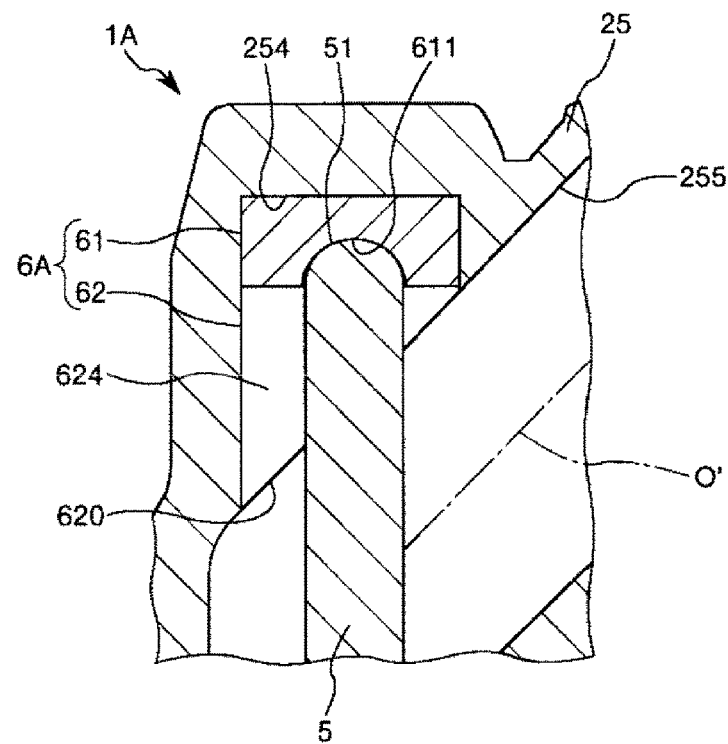
FIG. 6 is an enlarged cross-sectional view of a centrifugal pump according to a second embodiment of the present invention.
Figure 7:
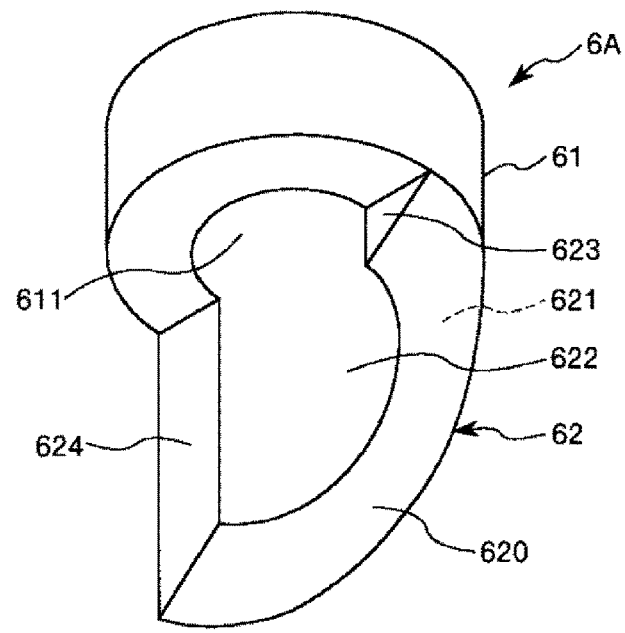
FIG. 7 is a perspective view of a first bearing illustrated in FIG. 6.

FIG. 6 is an enlarged cross-sectional view of a centrifugal pump (second embodiment) according to the present invention. FIG. 7 is a perspective view of a first bearing illustrated in FIG. 6.

Hereinafter, with reference to the views, the second embodiment of the centrifugal pump according to the present invention will be described. The points different from those of the aforementioned embodiment will be mainly described, and description of similar elements will be omitted.

The present embodiment is similar to the first embodiment except that the shape of the first bearing is different therefrom.

As illustrated in FIGS. 6 and 7, in a first bearing 6A of a centrifugal pump 1A, the protruding length of the protruding portion 62 is shorter than the protruding portion in the first embodiment. In addition, the apex surface 620 at the distal edge of the protruding portion 62 is positioned at the same distance in the radial direction as the inner peripheral surface 255 of the blood inlet port 25 from the central axis O'. Accordingly, as illustrated in FIG. 7, when the blood Q flowing down inside the blood inlet port 25 flows down in the vicinity of a boundary portion between the inner peripheral surface 255 of the blood inlet port 25 and the apex surface 620 of the first bearing 6A, the blood Q can smoothly flow down. Therefore, the first bearing 6A can be more reliably prevented from inhibiting a blood flow.

<Third Embodiment>

Figure 8:
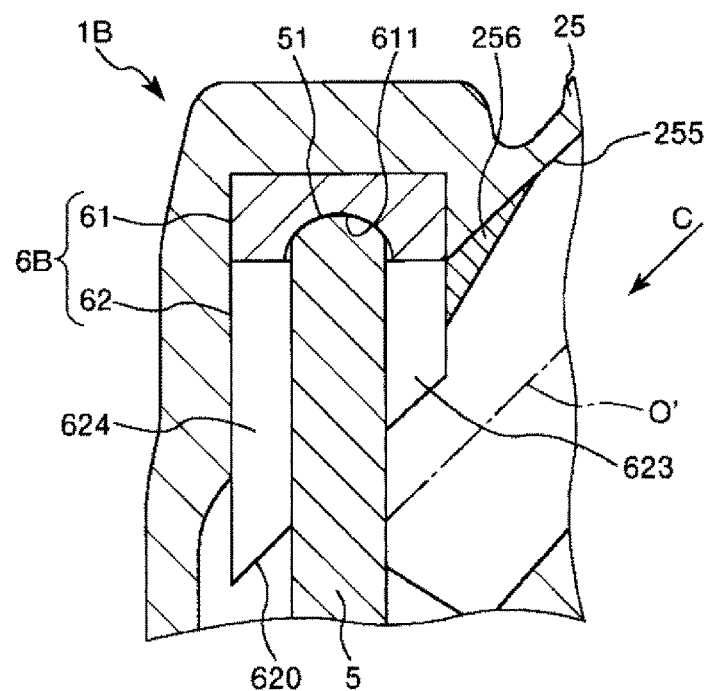
FIG. 8 is an enlarged cross-sectional view of a centrifugal pump according to a third embodiment of the present invention.
Figure 9:
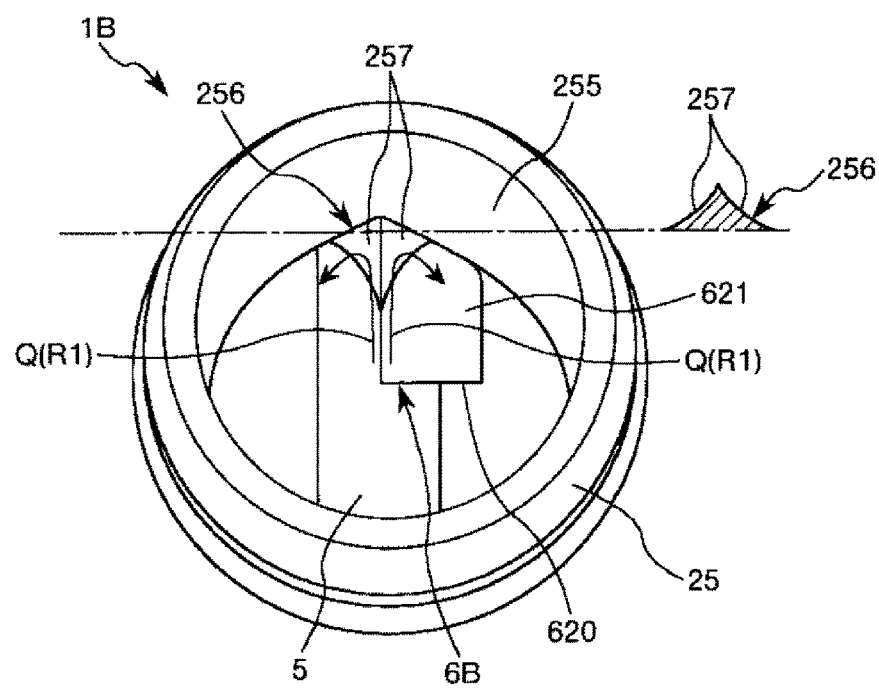
FIG. 9 is a view taken along arrow C in FIG. 8.

FIG. 8 is an enlarged cross-sectional view of a centrifugal pump (third embodiment), according to the present invention. FIG. 9 is a view viewed in the arrow C direction in FIG. 8.

Hereinafter, with reference to the views, the third embodiment of the centrifugal pump according to the present invention will be described. The points different from those of the aforementioned embodiments will be mainly described, and description of similar elements will be omitted. The present embodiment is substantially similar to the aforementioned first embodiment except that a flow straightening portion is provided. In particular, the flow straightening portion preferably has a substantially triangular profile which defines an apex extending longitudinally in the connection portion as described below.

As illustrated in FIGS. 8 and 9, a flow straightening portion 256 which is provided on the upstream side of a first bearing 6B and straightens the blood Q (first blood flow R1) is integrally formed in the blood inlet port 25 of a centrifugal pump 1B. The flow straightening portion 256 is provided so as to protrude toward the central axis O' side from the inner peripheral surface 255 of the blood inlet port 25. In addition, the flow straightening portion 256 extends along the central axis O'. Due to the flow straightening portion 256, the blood Q flowing down through the blood inlet port 25 flows on both sides via the flow straightening portion 256 (refer to FIG. 9). Accordingly, the blood Q flows down inside the blood inlet port 25 so as to bypass the first bearing 6 which is positioned on the downstream side of the rectification portion 256. Therefore, the blood Q can be more effectively prevented or restrained from being retained on the periphery of the first bearing 6. Therefore, a thrombus can be more effectively prevented or restrained from being formed in the outer peripheral portion of the first bearing 6.

In addition, the cross-sectional shape of the flow straightening portion 256 forms a substantially triangular having the apex on the central axis O' side. As illustrated in FIG. 9, in the flow straightening portion 256, the width and the protruding height gradually become smaller toward the upstream side. Accordingly, the first blood flow R1 is gently straightened from the upstream side.

Moreover, as illustrated in the auxiliary cross-sectional view of FIG. 9, a pair of side surfaces 257 of the flow straightening portion 256 is curved in a direction of approaching each other. Accordingly, the first blood flow R1 is more gently straightened from the upstream side.

According to such a configuration, the flow straightening portion 256 can more reliably exhibit the above-described effect.

In addition, the end portion of the straightening portion 256 on the downstream side is in contact with the outer peripheral portion of the first bearing 6B. Accordingly, for example, force which can be generated in the radial direction when the rotary body 3 rotates is applied to the first bearing 6B. Therefore, the straightening portion 256 can prevent the first bearing 6B from being deformed, that is, the straightening portion 256 can function as a reinforcement portion. As a result thereof, it is possible to achieve a long service life of the centrifugal pump 1B. Moreover, it is possible to reduce the influence to the first bearing 6B caused due to the fluid pressure of the blood Q, and thus, damage to blood can be reduced.

Hereinbefore, the centrifugal pump according to the present invention has been described with reference to the illustrated embodiments. The present invention is not limited thereto. Each of the portions configuring the centrifugal pump can be replaced with an arbitrarily configured portion which can exhibit a similar function. In addition, an arbitrarily configured element may be added thereto.

Note that, in each of the embodiments, the protruding portion is positioned so as to be closer to the upper side than the central axis of the blood inlet port in the cross section illustrated in FIG. 5. However, the present invention is not limited thereto. In the cross section illustrated in FIG. 5, the protruding portion may be positioned so as to be closer to the lower side than the central axis of the blood inlet port. In this case, the shaft member and the rotary body are configured to rotate counterclockwise when viewed from the first bearing side.

In addition, in the first embodiment and the second embodiment, the inclination portion (lower surface) of the first bearing is at the same distance in the radial direction of the blood inlet port as the inner peripheral surface of the blood inlet port from the central axis of the blood inlet port or is positioned so as to be closer to the central axis side in the radial direction of the blood inlet port than the inner peripheral surface of the blood inlet port. However, the present invention is not limited thereto. The inclination portion thereof may be positioned so as to be closer to a distal side from the central axis of the blood inlet port than the inner peripheral surface of the blood inlet port.

In addition, in the third embodiment, the flow straightening portion extends in the central axis direction of the blood inlet port. However, the present invention is not limited thereto. For example, flow straightening portions may be intermittently provided by causing the blood inlet port to be sparsely cutout in the longitudinal direction.

In addition, in the third embodiment, the cross-sectional shape of the flow straightening portion forms a substantial triangle. However, the present invention is not limited thereto. For example, the cross-sectional shape thereof may be a circle, a semicircle, a square, or a polygon having more sides.

In addition, in the third embodiment, the downstream side of the flow straightening portion is in contact with the first bearing. However, the present invention is not limited thereto. The downstream side thereof may be separated from the first bearing.

In addition, in the third embodiment, the flow straightening portion is integrally formed with the housing (blood inlet port). However, the present invention is not limited thereto. The flow straightening portion may be configured to be separate from the housing or may be integrally formed with the first bearing.

What is claimed is:
1. A centrifugal blood pump comprising:
a housing having a main body enclosing a pumping chamber, wherein the main body defines a blood inlet port which is formed so as to protrude from the housing main body and which communicates with the pumping chamber, and wherein the main body defines a blood outlet port which is provided at a position radial different from that of the blood inlet port;

a centrifugal force applying member that is rotatably accommodated inside the pumping chamber and rotates to apply centrifugal force to blood; and a support mechanism that supports the centrifugal force applying member such that the centrifugal force applying member can rotate with respect to the housing;

wherein the support mechanism comprises a shaft member which is installed along a rotational center axis of the centrifugal force applying member, a first bearing which is installed inside the blood inlet port and rotatably supports one end portion of the shaft member, and a second bearing which rotatably supports the other end portion of the shaft member; and wherein the first bearing is provided with a protruding portion which extends in an eccentric manner with respect to an end of the shaft member supported by the first bearing when viewed from an upstream position within the inlet port, wherein the protruding portion forms a semi-columnar shape which covers one half of a circumference of the shaft member.

2. The centrifugal pump according to claim 1 wherein the protruding portion shields a longitudinal side of the shaft member preventing a reverse flow of blood inside the blood inlet port.

3. The centrifugal pump according to claim 1:

wherein the blood inlet port includes a connection portion forming a cylindrical shape which is inclined with respect to the rotational center axis; and wherein the protruding portion has an inclined distal edge which inclines in a same direction as an inner peripheral surface of the connection portion of the blood inlet port.

4. The centrifugal pump according to claim 3:

wherein the blood inlet port is provided with a recessed portion of which an inner peripheral portion is formed to receive the first bearing; and wherein the inclined distal edge of the protruding portion is positioned at a distance equal to or less than a distance between the inner peripheral surface of the connection portion of the blood inlet port and a central axis of the connection portion of the blood inlet port.

5. The centrifugal pump according to claim 3 further comprising:

a flow straightening portion that is formed to protrude from the inner peripheral surface of the connection portion of the blood inlet port, wherein the flow straightening portion has a substantially triangular profile which defines an apex extending longitudinally in the connection portion.

6. The centrifugal pump according to claim 5 wherein the substantially triangular profile of the flow straightening portion has a width and a protruding height which gradually become smaller toward an upstream side.

7. A centrifugal blood pump comprising:

a housing having a main body enclosing a pumping chamber, wherein the main body defines a blood inlet port which is formed so as to protrude from the housing main body and which communicates with the pumping chamber, and wherein the main body defines a blood outlet port which is provided at a position radial different from that of the blood inlet port;

a centrifugal force applying member that is rotatably accommodated inside the pumping chamber and rotates to apply centrifugal force to blood; and a support mechanism that supports the centrifugal force applying member such that the centrifugal force applying member can rotate with respect to the housing;

wherein the support mechanism comprises a shaft member which is installed along a rotational center axis of the centrifugal force applying member, a first bearing which is installed inside the blood inlet port and rotatably supports one end portion of the shaft member, and a second bearing which rotatably supports the other end portion of the shaft member;

wherein the first bearing is provided with a protruding portion which extends in an eccentric manner with respect to an end of the shaft member supported by the first bearing when viewed from an upstream position within the inlet port;

wherein the blood inlet port includes a connection portion forming a cylindrical shape which is inclined with respect to the rotational center axis;

wherein the protruding portion has an inclined distal edge which inclines in a same direction as an inner peripheral surface of the connection portion of the blood inlet port; and wherein the housing includes a flow straightening portion that is formed to protrude from the inner peripheral surface of the connection portion of the blood inlet port, wherein the flow straightening portion has a substantially triangular profile which defines an apex extending longitudinally in the connection portion, and wherein the substantially triangular profile of the flow straightening portion has a width and a protruding height which gradually become smaller toward an upstream side.

* * * * *